(12) United States Patent
Backman et al.

(10) Patent No.: US 6,355,269 B1
(45) Date of Patent: Mar. 12, 2002

(54) ORAL COMPOSITIONS OF LEVOSIMENDAN

(75) Inventors: Maarit Backman, Helsinki (FI); Ilkka Larma, Springfield, NJ (US); Saila Antila, Helsinki; Lasse Lehtonen, Espoo, both of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/509,205

(22) PCT Filed: Sep. 24, 1998

(86) PCT No.: PCT/FI98/00753

§ 371 Date: Jun. 8, 2000

§ 102(e) Date: Jun. 8, 2000

(87) PCT Pub. No.: WO99/16443

PCT Pub. Date: Apr. 8, 1999

(30) Foreign Application Priority Data

Sep. 26, 1997 (FI) .................................................. 973804

(51) Int. Cl.[7] .......................... A61K 9/20; A61K 31/50; C07D 237/02
(52) U.S. Cl. ........................ 424/464; 514/247; 544/239
(58) Field of Search ........................ 424/464; 514/247; 544/239

(56) References Cited

U.S. PATENT DOCUMENTS 5,569,657 A * 10/1996 Nore et al. .................. 514/247
6,180,789 B1    1/2001 Timmerbacka

FOREIGN PATENT DOCUMENTS

| EP | 0 383 449 | 8/1990 |
| WO | WO 92/12135 | 7/1992 |
| WO | Wo 93/21921 | 11/1993 |
| WO | WO 97/35841 | 10/1997 |
| WO | WO 98/01111 | 1/1998 |

* cited by examiner

Primary Examiner—Thurman K. Page
Assistant Examiner—Blessing Fubara
(74) Attorney, Agent, or Firm—Finnegan, Henderson, Farabow, Garrett & Dunner, L.L.P.

(57) ABSTRACT

A composition for oral administration comprising a substantially pure crystalline polymorphic form (I) of levosimendan as an active ingredient together with a pharmaceutically acceptable carrier is described. Polymorphic form (I) of levosimendan is rapidly absorbed from the gastrointestinal tract and is useful in the treatment of congestive heart disease.

4 Claims, 1 Drawing Sheet

ORAL COMPOSITIONS OF LEVOSIMENDAN

This application is a national stage filing of PCT International Application No. PCT/FI98/00753, filed Sep. 24, 1998, the content of which is incorporated herein by reference.

TECHNICAL FIELD

The present invention relates to pharmaceutical compositions for oral administration comprising substantially pure polymorphic form I of levosimendan, the (−) enantiomer of [[4-(1,4,5,6-tetrahydro-4-methyl-6-oxo-3-pyridazinyl) phenyl]hydrazono]propanedinitrile, as an active ingredient. Levosimendan is useful in the treatment of congestive heart failure.

BACKGROUND OF THE INVENTION

The racemic mixture of [[4-(1,4,5,6-tetrahydro-4-methyl-6-oxo-3-pyridazinyl)phenyl]hydrazono]propanedinitrile (I) has been described earlier in the applicant's European Patent No. 383449 B1. It was shown that compound (I) is potent in the treatment of congestive heart failure and has significant calcium dependent binding to troponin.

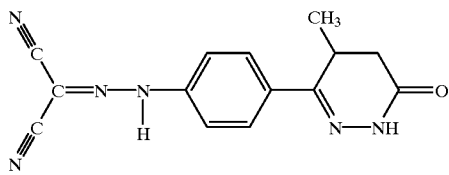

I

Optically active enantiomers of (I) have been earlier described in the applicant's European Patent No. 565546 B1. It was shown that the cardiotonic potency is predominantly due to the (−) enantiomer of (I), i.e. levosimendan.

Oral administration of levosimendan has proved difficult since levosimendan is susceptible to metabolization in the lower gastrointestinal tract by intestinal bacteria. The metabolites formed in the lower gastrointestinal tract may contribute to the observed side effects of orally administered levosimendan, such as headache and palpitation. Therefore methods and compositions for administering levosimendan orally which would avoid or reduce the accumulation of levosimendan in the lower gastrointestinal tract would be highly desirable.

SUMMARY OF THE INVENTION

It has now been found that levosimendan is rapidly dissolved and absorbed into plasma from oral compositions which comprise substantially pure crystalline polymorphic form I of levosimendan as the active ingredient. The rapid absorption reduces the accumulation of levosimendan in the lower gastrointestinal tract and thereby reduces gastrointestinal metabolization of levosimendan.

Thus the present invention provides an oral composition comprising a substantially pure crystalline polymorphic form I of levosimendan as the active ingredient together with a pharmaceutically acceptable carrier.

DETAILED DESCRIPTION

Figure 1:
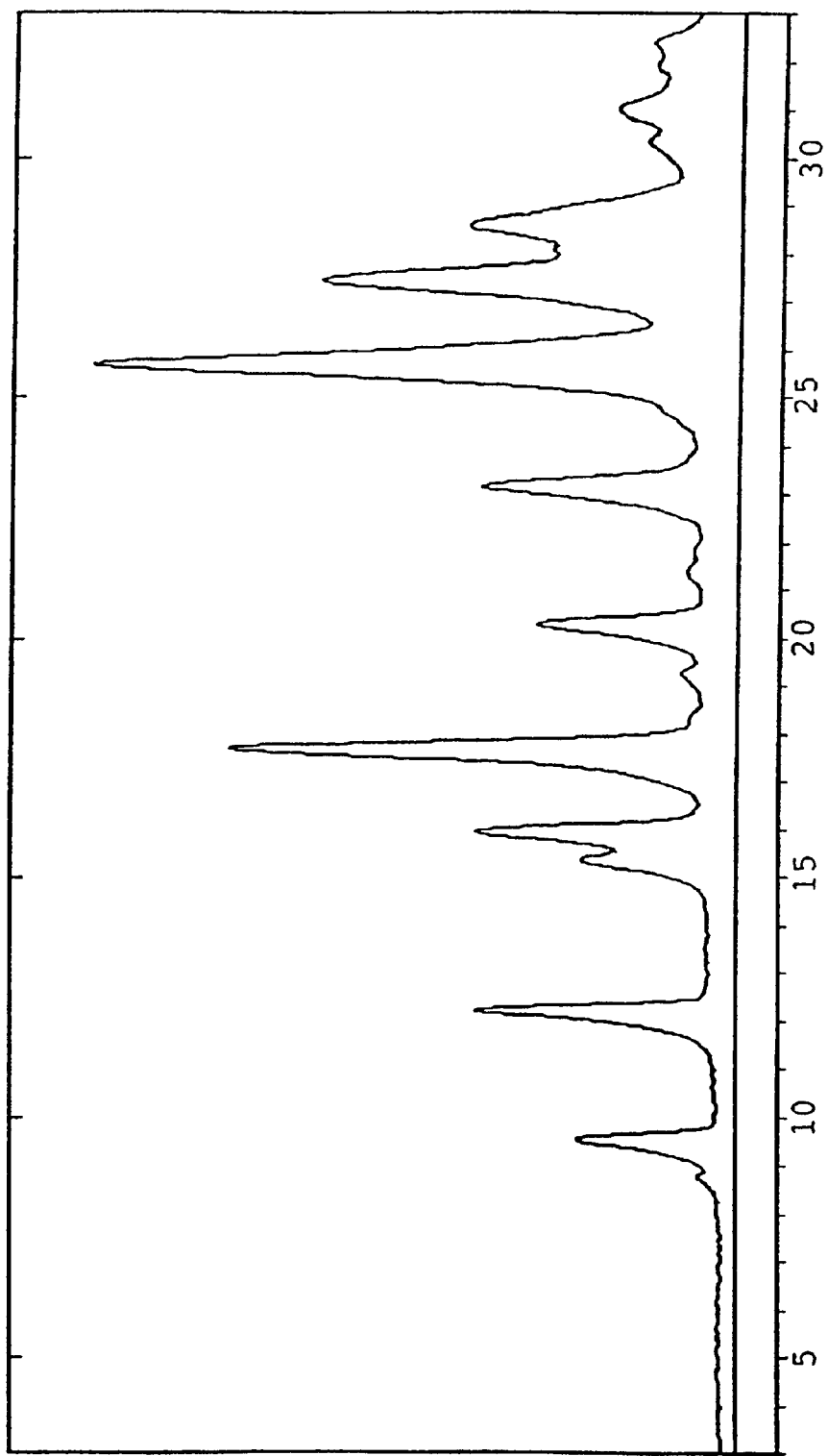
FIG. 1 is the X-ray powder diffraction pattern in 3–33 2θ° range of the polymorphic form I of (−)-[[4-(1,4,5,6-tetrahydro-4-methyl-6-oxo-3-pyridazinyl)-phenyl] hydrazono]propanedinitrile

The term "substantially pure crystalline polymorphic form I of levosimendan" means here (−)-[[4-(1,4,5,6-tetrahydro-4-methyl-6-oxo-3-pyridazinyl)phenyl] hydrazono]propanedinitrile of which at least about 90%, preferably at least 95%, and more preferably at least 99% per weight is in the form of crystalline polymorph I.

Crystalline polymorphic form I of levosimendan can be prepared from compound (II) by resolution of the racemic material in two different synthesis stages.

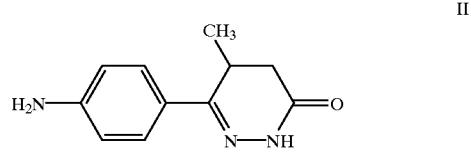

II

The racemic compound (II) can be synthesized by methods known in the literature (J. Med. Chem., 17, 273–281 (1974)).

The initial resolution step comprises reacting the racemic mixture of (II) with D- or L-tartaric acid in ethyl acetate solvent. Advantageously the ethyl acetate solvent contain from 0 to about 6 w-%, preferably from 2 to 4 w-%, more preferably about 3 w-%, of water. It is preferred to use D- or L-tartaric acid and compound (II) in about equimolar amounts. The diastereomeric salts of (−) 6-(4-aminophenyl)-4,5-dihydro-5-methyl-3(2H)-pyridazinone with D-tartaric acid or corresponding (+) 6-(4-aminophenyl)-4,5-dihydro-5-methyl-3(2H)-pyridazinone with L-tartaric acid crystallize from ethyl acetate in good yield. The crystalline diastereomeric salt can be filtered and the free base liberated by basifying the salt with e.g. potassium carbonate solution or ammonia. The mother liquid can be recovered after filtering and be further treated in order to recover the enantiomer which was not previously removed by precipitation. The treatment may comprise e.g. cooling the mother liquid and recovering the resulting crystalline diastereomeric salt.

Typically the product obtained by the above described method contains about 90 w-% of the desired enantiomer of (II). The purity of the product can be increased to about 96 w-% by recrystallization. Acetonitrile is the preferred recrystallization solvent. For example, the product which is enriched in (−) enantiomer is recrystallized by adding the product to acetonitrile solvent, refluxing the mixture and filtering precipitate. The filtrate is concentrated, if necessary, and cooled in order to crystallize the (−) enantiomer of (II).

Partial resolution of compound (II) can be obtained using other solvent systems than ethyl acetate. Such solvents include isopropanol, isobutanol, isopropyl acetate, butyl acetate, acetone and acetonitrile. Also the use of other resolving acids than D- or L-tartaric acid can result in partial resolution of compound (II), e.g. benzoic acid or sulphuric acid. However, the method of using D- or L-tartaric acid in ethyl acetate or aqueous ethyl acetate solvent provides the highest optical purities for compound (II).

The (−) enantiomer of [[4-(1,4,5,6-tetrahydro-4-methyl-6-oxo-3-pyridazinyl)phenyl]hydrazono]propanedinitrile (I) is prepared from 6-(4-amino-phenyl)-4,5-dihydro-5-methyl-3(2H)-pyridazinone (II) which is enriched in (−) enantiomer by allowing (II) to react with sodium nitrite and malononitrile in acidic conditions as described in EP 383449 B1. Compound (I) which is enriched in (−) enantiomer is then recovered.

The minor component in a partly enriched enantiomer mixture of compound (I) can be filtered out from acetone leaving the rest of the major component in solution. This allows recovering the substantially pure (−) enantiomer of (I) from the mother solution by crystallization.

Thus, the previously recovered compound (I) which is enriched in (−) enantiomer is suspended in acetone solvent, which preferably contains up to 2 w-% of water. The mixture is refluxed and the precipitate is filtered. The filtrate is then concentrated, if necessary, and cooled to about 0–(−5)° C. The precipitated crystalline (−) enantiomer of (I) is recovered. The product contains typically more than 99 w-% of the desired (−) enantiomer of (I).

The crystallographical purity of the above obtained polymorphic form I of compound (I) can be, if desired, improved by heating the obtained (−) enantiomer of (I) at a temperature of at least about 70° C. for a time period necessary for the formation of crystallographically pure polymorphic form I. The suitable temperature is typically within the range of 70–160° C., preferably 80–130° C. The time period is typically within the range of 1–48 h, preferably 4–24 h. This treatment may be part of the drying process of the product and may be carried out in vacuum.

The polymorphic form I of (−)-[[4-(1,4,5,6-tetrahydro-4-methyl-6-oxo-3-pyridazinyl)phenyl]hydrazono]propanedinitrile is characterized by the X-ray crystallography. The X-ray powder diffraction pattern of the polymorphic form I in 3–33 2θ° range is in FIG. 1 and the crystallographic data in Table 1.

The diffraction pattern was measured by the X-ray powder diffraction (XRPD) equipment, Siemens D 500 (Siemens AG, Karlsruhe, Germany). A copper target X-ray (wavelength 0.1541 nm) tube was operated with the power of 40kV×40 mA. For X-ray powder diffraction analysis the samples were mounted by loosely pressing about 500 mg of the powder to the specific cylindrical sample stage which has a diameter of 20 mm and height of approximately 2 mm. Mathematical evaluation of diffraction patterns was performed with aid of Diffrac AT V3.1 software package. Main characteristics of the diffraction patterns as 2θ-values and relative peak intensities were produced as out-put data.

TABLE 1

X-ray diffraction angles (2θ °) and corresponding relative intensity values (only %-values >5%) of polymorphic form I.

| 2θ angle(°) | Relative intensity (%) |
| --- | --- |
| 8.7 | 5 |
| 9.5 | 23 |
| 12.2 | 34 |
| 15.4 | 25 |
| 15.9 | 40 |
| 17.7 | 72 |
| 18.4 | 8 |
| 19.2 | 9 |
| 20.3 | 27 |
| 21.4 | 8 |
| 21.8 | 8 |
| 23.1 | 36 |
| 24.6 | 12 |
| 25.7 | 100 |
| 27.4 | 64 |

The relative intensity values may vary remarkably because of different orientation of crystals. Therefore, the relative intensity values given in Table 1 can be regarded as representative only for, e.g. non-micronized powder.

The present invention provides a composition for oral administration comprising a substantially pure crystalline polymorphic form I of levosimendan as the active ingredient together with a pharmaceutically acceptable carrier. The compositions of the invention include solid compositions in the form of e.g. tablets, dragees, capsules, powders and granules. The contents of the active compound in the composition of the invention is generally from about 0.01 to 100%, preferably from 0.1 to 20%, most preferably from 0.5 to 10% per weight. In general levosimendan is administered orally to man in doses from about 0.1 to 10 mg, preferably from 0.5 to 5 mg once or several times a day depending on the age, body weight and condition of the patient.

The compositions of the invention can be prepared by mixing substantially pure crystalline polymorphic form I of levosimendan together with pharmaceutically acceptable carriers. Pharmaceutically acceptable carriers include those which are used according to standard pharmaceutical practice and which are compatible with the active ingredient. For oral administration in tablet form, suitable carriers and excipients include lactose, corn starch, magnesium stearate, calcium phosphate and talc. For oral administration in capsule form, useful carriers and excipients include lactose, corn starch, magnesium stearate and talc. Capsules can be prepared by mixing the active ingredient with the carriers and excipients and placing the powdery mixture in capsules, e.g. hard gelatin capsules. Tablets can be prepared by mixing the active ingredient with the carriers and excipients and compressing the powdery mixture into tablets.

The following examples are meant to further illustrate the invention without limitation.

EXAMPLE 1

Pharmaceutical Example

| Hard gelatin capsule size 3 | |
| --- | --- |
| Levosimendan (polymorph I) | 2.0 mg |
| Lactose | 198 mg |

EXAMPLE 2

Pharmacokinetic Study

Pharmacokinetic parameters of two different polymorphs, (I) and (II), of levosimendan in healthy volunteers after a single oral dose of 2 mg of levosimendan capsule was studied. The formulations of hard gelatin capsules (size 3) A and B were the following:

| Capsule A: | |
| --- | --- |
| Levosimendan (polymorph I) | 2.0 mg |
| Lactose | 198 mg |
| Capsule B | |
| Levosimendan (polymorph II) | 2.0 mg |
| Lactose | 198 mg |

The results of the pharmakinetic study are presented in Table 2 and 3. The small value of $T_{max}$ indicates rapid absorption of the drug into plasma.

TABLE 1

Pharmacokinetic parameters after a single oral dose of capsule A to healthy subjects 1–9.

| Subject | $C_{max}$ (ng/ml) | $T_{max}$ (h) | $t_{½}$ (h) | AUC (ng h/ml) |
|---|---|---|---|---|
| 1 | 67.9 | 0.75 | 0.82 | 97 |
| 2 | — | — | — | — |
| 3 | 82.0 | 1.00 | 0.83 | 166 |
| 4 | — | — | — | — |
| 5 | 112 | 0.33 | 0.76 | 131 |
| 6 | 92.1 | 0.75 | 0.86 | 155 |
| 7 | 79.9 | 1.25 | 0.81 | 185 |
| 8 | 172 | 0.50 | 0.81 | 191 |
| 9 | 125 | 0.50 | 0.88 | 135 |
| Mean | 104 | 0.73 | 0.82 | 151 |
| SD | 36 | 0.32 | 0.04 | 33 |
| SEM | 13 | 0.12 | 0.01 | 12 |

TABLE 2

Pharmacokinetic parameters after a single oral dose of capsule B to healthy subjects 1–9.

| Subject | $C_{max}$ (ng/ml) | $T_{max}$ (h) | $t_{½}$ (h) | AUC (ng h/ml) |
|---|---|---|---|---|
| 1 | 91.1 | 0.50 | 0.78 | 109 |
| 2 | 76.0 | 1.00 | 0.65 | 123 |
| 3 | 112 | 1.00 | 0.72 | 151 |
| 4 | 111 | 0.33 | 0.84 | 134 |
| 5 | 88.4 | 1.50 | 0.67 | 174 |
| 6 | 150 | 0.50 | 0.77 | 178 |
| 7 | — | — | — | — |
| 8 | 89.7 | 0.75 | 0.86 | 176 |
| 9 | 45.0 | 2.50 | 0.76 | 121 |
| Mean | 95 | 1.01 | 0.76 | 146 |
| SD | 31 | 0.71 | 0.07 | 28 |
| SEM | 11 | 0.25 | 0.03 | 10 |

EXAMPLE 3

Preparation of (−)-6-(4-aminophenyl)-4,5-dihydro-5methyl-3(2H)-pyridazinone 100 g of racemic 6-(4-aminophenyl)-4,5-dihydro-5-methyl-3(2H)-pyridazinone was added to 2997 ml of ethyl acetate, 94.4 ml of water, 77.8 g of D-tartaric acid and 1.0 g of D-tartaric salt of (−)-6-(4-aminophenyl)-4,5-dihydro-5-methyl-3(2H)-pyridazinone under nitrogen. The mixture was stirred in 25° C. for 1.5 h. The mixture was then heated to 65° C. and stirred for 2 h. The precipitate was filtered hot and washed with 561 ml of ethyl acetate. The precipitate was mixed with 400 ml of water and pH of the mixture was adjusted to 9–10 with NH₃. The mixture was cooled to 0° C. and stirred for 2 h. The precipitate was filtered, washed three times with 322 ml of cold water and dried in vacuum in 50° C. Yield was 35 g and the ratio of (−/+) enantiomers 93/7%. The product (35 g) was further added to 777 ml of acetonitrile and 2.0 g of celite under nitrogen. The precipitate was filtered hot and washed with 33 ml of acetonitrile which was added to the filtrate. 253 ml of acetonitrile was distilled from the filtrate and the remaining mixture was cooled to −5° C. The precipitate was filtered, washed with 76 ml of acetonitrile and dried in vacuum in 50° C. Yield 24.5 g. Ratio of (−/+) enantiomers 96/4%.

EXAMPLE 4

Preparation of (−)-[[4-(1,4,5,6-tetrahydro-4-methyl-6-oxo-3-pyridazinyl)phenyl]hydrazono]propanedinitrile The 6-(4-aminophenyl)-4,5-dihydro-5-methyl-3(2H)-pyridazinone obtained in previous Example with (−/+) resolution % of 96/4 was treated with sodium nitrite and malononitrile as described in the European Patent No. 383449 B1. 10 g of the recovered [[4-(1,4,5,6-tetrahydro-4-methyl-6-oxo-3-pyridazinyl)phenyl]hydrazono]propanedinitrile with (−/+) resolution % of 96/4 was added to 150 ml of acetone, 0.9 ml of water, 0.2 g of activated carbon and 0.4 g of Celite. The mixture was refluxed for 1 h and filtered hot. The precipitate was washed with 10 ml of hot acetone which was added the to the filtrate. The filtrate was refluxed for 30 min. 61 ml of acetone was distilled from the filtrate and the remaining mixture was cooled to 0–(−5)° C. The mixture was filtered and washed with 10 ml of cold acetone. The crystalline product was dried in vacuum in 100° C. for 5 h. The product contained over 99% of the desired (−) enantiomer and the yield was 6.8 mg. The product was substantially pure crystalline polymorphic form I.

The enantiomeric purities of the products were determined by the high performance liquid chromatography (HPLC). The enantiomers of compound (II) were separated by using a cellulose-type chiral column (Chiralcel OJ 25×0.46 cm). The mobile phase consisted of ethanol. The flow rate was 0.5 ml/min. The enantiomers of compound (I) were separated by using a β-cyclodextrin column (Cyclobond I Beta, 4.6×250 mm). The mobile phase consisted of 36% methanol in water buffered to pH 6.0 with 1% triethylammonium acetate. The flow rate was 0.8 ml/min.

We claim:

1. A composition for oral administration, comprising substantially pure crystalline polymorphic form I of levosimendan as an active ingredient together with a pharmaceutically acceptable carrier, wherein the crystalline polymorphic form I of levosimendan is characterized by the X-ray diffraction pattern having the following peak positions:

| 2θ angle (°) |
|---|
| 8.7 |
| 9.5 |
| 12.2 |
| 15.4 |
| 15.9 |
| 17.7 |
| 18.4 |
| 19.2 |
| 20.3 |
| 21.4 |
| 21.8 |
| 23.1 |
| 24.6 |
| 25.7 |
| 27.4 | wherein the amount of the active ingredient in the composition is from 0.1 to 20% per weight of the composition.

2. A composition as claimed in claim 1, wherein the amount of the active ingredient in the composition is from 0.5 to 10% per weight of the composition.

3. A composition for oral administration, comprising substantially pure crystalline polymorphic form I of levosimendan as an active ingredient together with a pharmaceutically acceptable carrier, wherein the crystalline polymorphic form I of levosimendan is characterized by the X-ray diffraction pattern having the following peak positions:

| 2θ angle (°) |
|---|
| 8.7 |
| 9.5 |
| 12.2 |
| 15.4 |
| 15.9 |
| 17.7 |
| 18.4 |
| 19.2 |
| 20.3 |
| 21.4 |
| 21.8 |
| 23.1 |
| 24.6 |
| 25.7 |
| 27.4 | wherein the amount of the active ingredient is 0.1 to 10 mg.

4. A composition for oral administration, comprising substantially pure crystalline polymorphic form I of levosimendan as an active ingredient together with a pharmaceutically acceptable carrier, wherein the crystalline polymorphic form I of levosimendan is characterized by the X-ray diffraction pattern having the following peak positions:

| 2θ angle (°) |
|---|
| 8.7 |
| 9.5 |
| 12.2 |
| 15.4 |
| 15.9 |
| 17.7 |
| 18.4 |
| 19.2 |
| 20.3 |
| 21.4 |
| 21.8 |
| 23.1 |
| 24.6 |
| 25.7 |
| 27.4 | wherein the pharmaceutically acceptable carrier is lactose.

* * * * *